United States Patent [19]
Hacksell et al.

[11] Patent Number: 5,376,687
[45] Date of Patent: Dec. 27, 1994

[54] BICYCLIC AMINO-SUBSTITUTED COMPOUNDS

[75] Inventors: Uli A. Hacksell; Sven-Erik Hillver, both of Uppsala, Sweden

[73] Assignee: Aktiebolaget Astra, Sodertalje, Sweden

[21] Appl. No.: 741,438

[22] PCT Filed: Dec. 5, 1990

[86] PCT No.: PCT/SE90/00806
§ 371 Date: Aug. 7, 1991
§ 102(e) Date: Aug. 7, 1991

[87] PCT Pub. No.: WO90/07490
PCT Pub. Date: Jul. 12, 1990

[30] Foreign Application Priority Data
Dec. 7, 1989 [SE] Sweden ............... 8904127-1

[51] Int. Cl.$^5$ ............... A61K 31/135; C07C 217/74
[52] U.S. Cl. ............... 514/657; 564/428
[58] Field of Search ............... 564/428; 514/657

[56] References Cited

U.S. PATENT DOCUMENTS
5,225,596  7/1993  Carlsson et al. ............... 564/428

FOREIGN PATENT DOCUMENTS
0041488 12/1981 European Pat. Off. .
0222996  5/1987 European Pat. Off. .
0334538  9/1989 European Pat. Off. .
0343830 11/1989 European Pat. Off. .
2803582  8/1979 Germany .
9007490  7/1990 WIPO .
9015047 12/1990 WIPO .

OTHER PUBLICATIONS
DeMarinss et al, Chemical Abstracts, vol. 96 (1982) 51940w.
Heible et al, chemical Abstracts, vol. 97 (1982) 16659k.
Holz et al, Chemical Abstracts, vol. 98 (1983) 11098n.
Singh et al, Chemical Abstracts, vol. 100 (1984) 79479c.
Weinstock et al, J. Med. Chem., vol. 29 (1986) pp. 1615-1627.
Arvidsson, et al. 1981 "8–Hydroxy-2–(di-n–propylamino) tetralin, a New Centrally Acting 5-Hydroxytryptamine Receptor Agonist" J. Med. Chem. 24:921-923.
Middlemiss, et al. 1983 "8–Hydroxy-2(di-n–propylamino)-tetralin Discriminates between Subtypes of the 5-HT$_1$ Recognition Site" Eur. J. Pharm. 90: 151-153.

*Primary Examiner*—Richard L. Raymond
*Attorney, Agent, or Firm*—White & Case

[57] ABSTRACT

A compound of formula (I), wherein X is O, CH$_2$, S, SO or SO$_2$; R is F or Cl; R$_1$ is H, C$_1$-C$_6$ alkyl or C$_2$-C$_6$ alkenyl; R$_2$ is H, C$_1$-C$_6$ alkyl or C$_2$-C$_6$ alkenyl; R$_3$ is H, C$_1$-C$_6$, alkyl, a pharmaceutically acceptable salt thereof, an enantiomer thereof, and a pharmaceutically acceptable salt of said enantiomer for use in therapy. A pharmaceutical preparation containing as active ingredient any one of said compounds. A process for the preparation of a compound of formula (I).

13 Claims, No Drawings

BICYCLIC AMINO-SUBSTITUTED COMPOUNDS

DESCRIPTION

1. Field of the Invention

The present invention relates to the (S)enanantiomers of new substituted-3-amino-chromans, thiochromans, and tetralins and salts thereof, processes for their preparation, pharmaceutical compositions containing said therapeutically active compounds as well as new intermediates useful in the preparation of the therapeutically active compounds and to the use of said active compounds in therapy.

An object of the invention is to provide compounds for therapeutic use, especially compounds having a therapeutic activity via the central nervous system (CNS). A further object is to provide compounds having a selective effect on 5-hydroxy-tryptamine receptors in meals including man.

2. Prior Art

Therapeutically useful 3-amino-dihydro-[1]-benzopyrans and benzothiopyrans having effect on 5-hydroxy-tryptamine neurons in meals are disclosed in EP 0222 996.

These compounds are defined by the formula

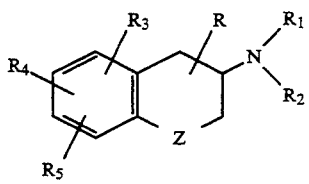

wherein
Z is 0 or S;
R is hydrogen or lower alkyl;
R₁ is hydrogen, lower alkyl or aryl lower alkyl;
R₂ is hydrogen, lower alkyl or aryl lower alkyl; or R₁ and R₂ together form a ring with 4–6 carbon atoms;
R₃ is hydrogen, hydroxy, lower alkoxy, aryl lower alkoxy, acyloxy or aryloxy or when Z is S and R₃ is hydroxy, lower alkoxy, aryl lower alkoxl, acyloxy or aryloxy when Z is O and R₃ is in 5- or 8-position when Z is O;
R₄ and R₅ are independently hydrogen, lower alkyl or halogen, and mono- or di-S-oxides thereof when Z is S, and pharmaceutically acceptable salts thereof.

DISCLOSURE OF THE INVENTION

The object of the present invention is to obtain new compounds which have a high affinity to the 5-hydroxy-tryptamine receptors in the central nervous system at the same time as they act as agonists, partial agonists or antagonists on the serotonin receptors.

Thus, a group of new compounds of the formula I of the present invention, salts and prodrugs thereof are useful in therapeutic treatment of 5-hydroxy-tryptamine mediated states and disorders such as depression, anxiety, anorexia, senile dementia, Alzheimer's disease, migraine, termoregulator and sexual disturbances. Further aspects of the invention are related to the use of the compounds, enantiomers and salts thereof in pain control and in modulation of the cardiovascular system.

Thus, the invention provides compounds of the formula

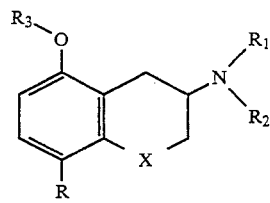

wherein
X is O, CH₂, S, SO or SO₂
R is F or Cl
R₁ is H, C₁–C₆ alkyl or C₂–C₆ alkenyl
R₂ is H, C₁–C₆ alkyl or C₂–C₆ alkenyl
R₃ is H, C₁–C₆ alkyl C₁–C₆ alkyl in formula I representing straight, branched and ayclic alkyl groups having 1 to 6 carbon atoms, for example methyl, ethyl, n-propyl, i-propyl, n-buryl, i-butyl, t-butyl, n-pentyl, i-pentyl, t-pentyl, n-hexyl, i-hexyl, cyclopropyl, cyclobutyl, cyclopentyl, cyclohexyl, methylcyclopropyl, ethylcyclopropyl, methylcyclobutyl. Preferred alkyl groups have 1 to 4 carbon atoms.

C₂–C₆ alkenyl in formula I representing straight or branched carbon atom chains having 2 to 6 carbon atoms and containing one or two double bonds, for example allyl, proponyl, isopropenyl, butenyl, isobutenyl, pentenyl, isopentenyl. Preferred alkenyl groups have 2 to 4 carbon atoms and one double bond.

R₁ and R₂ may together form a 5- or 6-membered ring containing 1 or 2 heteroatoms selected from N, O and S.

A further aspect of the invention is a pharmaceutical preparation containing as active ingredient a compound according to formula II.

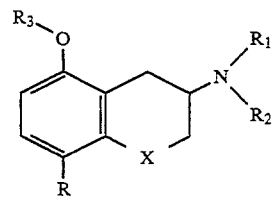

wherein
X is O, CH S, SO or SO₂
R is F or Cl
R₁ is H, C₁–C₆ alkyl or C₂–C₆ alkenyl
R₂ is H, C₁–C₆ alkyl or C₂–C₆ alkenyl
R₃ is H, C₁–C₆ alkyl C₁–C₆ alkyl in formula II representing straight, branched and cyclic alkyl groups having 1 to 6 carbon atoms, for example methyl, ethyl, n-propyl, i-propyl, n-buryl, i-buryl, t-butyl, n-pentyl, i-pentyl, t-pentyl, n-hexyl, i-hexyl, cyclopropyl, cyclobutyl, cyclopentyl, cyclohexyl, methylcyclopropyl, ethylcyclopropyl, methylcyclobutyl. Preferred alkyl groups have 1 to 4 carbon atoms.

C₂–C₆ alkenyl in formula II representing straight or branched carbon atom chains having 2 to 6 carbon atoms and containing one or two double bonds, for example allyl, propenyl, isopropenyl, butenyl, isobutenyl, pentenyl, isopentenyl. Preferred alkenyl groups have 2 to 4 carbon atoms and one double bond.

R₁ and R₂ may together form a 5- or 6-membered ring containing 1 or 2 heteroatoms selected from N, O and S.

Especially preferred are compounds according to the invention where R is fluorine and $R_1$, $R_2$, $R_3$ are selected among methyl, ethyl and n-propyl.

The absolute configuration of (+)—X—HBr has been established by X-ray crystallography (Ingeborg Csöregh, unpublished results) to be R.

It is the S enantiomers of the compounds according to the invention that show the 5-$HT_{1A}$ receptor antagonist effect. This is suggested by the fact that (S)—X in the rat model inhibits (R)—XXIV ((S)—8-hydroxy-2-(dipropylamino)-tetralin, ((S)-8-OH DPAT) induced biochemical and behavioral changes in a dose-dependent manner. Both (S)-XXIV and (R)-XXIV are known to be potent 5-$HT_{1A}$-receptor agonists. In contrast, racemic X is inactive in functional assays which should be due to (R)-X exhibiting pharmacological characteristics common to other tetralin-based 5-$HT_{1A}$-receptor agonists.

(S)-X (32 μmoles/kg, s.c.) does not significantly affect 5-HTP levels in rats not pretreated with reserpine or the behaviour of reserpine-pretreated rats. It does, however, displace (S)-XXIV from 5-$HT_{1A}$-receptors (Table 1).

In addition, the behavioral effects of (R)-XXIV (μmol/kg, s.c. ) in reserpinized rats are completely blocked by pretreatment with (S)-2 (10 μmol/kg, s.c., given 10 min before). Pretreatment with (S)-X 2 h before attenuates the (R)-XXIV-induced behavious but no blockade is observed when (S)-X is being given 4 h before (R)-XXIV. This antagonism is equally effective after pretreatment with the $D_2$-receptor antagonist haloperindol (2 mg/kg, i.p.).

TABLE 1

Affinities of the Enantiomers of X at [³H] 8-OH DPAT Labelled 5-$HT_{1A}$-Sites.

| compd | 5-$HT_{1A}$-sites | |
|---|---|---|
| | $K_1$, nM | $N_H$ |
| (R)-X | 6.1 | 0.89 |
| (S)-X | 52 | 0.49 |
| (±)-XXIV | 1.0 | 0.92 |

Method according to Liu, Y.; Mellin, C.; Björk, L.; Svensson, B.; Csöregh, I,; Helander, A.; Kenne, L.; Andén, N.-E.; Hacksell, U. *J. Med. Chem.* 1989, 32, 2311-3218.

Formulae of individual compounds according to the invention are shown in Formula scheme III.

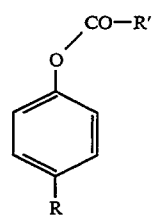

| | |
|---|---|
| R = F, R' = $CH_2CH_2Cl$ | I |
| R = Cl, R' = CH=$CH_2$ | XII |
| R = Cl, R' = $CH_2CH_2Cl$ | XXIII |

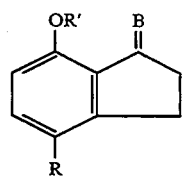

-continued

| | |
|---|---|
| R = F, R' = H, B = O | II |
| R = F, R' = $CH_3$, B = O | III |
| R = Cl, R' = H, B = O | XI |
| R = Cl, R' = $CH_3$, B = O | XIV |
| R = F, R' = $CH_3$, B = $CH_2$ | IV |
| R = Cl, R' = $CH_3$, B = $CH_2$ | XV |

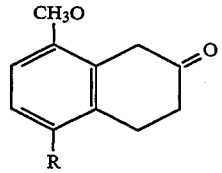

| | |
|---|---|
| R = F | V |
| R = Cl | XVI |

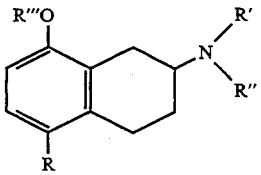

| | |
|---|---|
| R = F, R' = $CH_2Ph$, R" = H, R'" = $CH_3$ | VI |
| R = Cl, R' = $CH_2Ph$, R" = H, R'" = $CH_3$ | XVII |
| R = F, R' = H, R" = H, R'" = $CH_3$ | VII |
| R = Cl, R' = H, R" = H, R'" = $CH_3$ | XVIII |
| R = F, R' = $C_3H_7$, R" = $C_3H_7$, R'" = $CH_3$ | VIII |
| R = Cl, R' = $C_3H_7$, R" = $C_3H_7$, R'" = $CH_3$ | XIX |
| R = F, R' = $C_3H_7$, R" = H, R'" = $CH_3$ | IX |
| R = Cl, R' = $C_3H_7$, R" = H, R'" = $CH_3$ | XX |
| R = F, R' = $C_3H_7$, R" = $C_3H_7$, R'" = H | X |
| R = Cl, R' = $C_3H_7$, R" = $C_3H_7$, R'" = H | XXI |
| R = F, R' = $CH_2Ph$, R" = $C_3H_7$, R'" = $CH_3$ | XI |
| R = Cl, R' = $CH_2Ph$, R" = $C_3H_7$, R'" = $CH_3$ | XXII |

Pharmaceutical Preparations

According to the present invention the compounds of the formula I will normally be administered orally, rectally or by injection, in the form of pharmaceutical preparations comprising the active ingredient either as a free base or a pharmaceutically acceptable non-toxic salt, e.g. the hydrochloride, hydrobromide, lactate, acetate, phosphate, sulphate, sulphamate, citrate, tartrate, oxalate and the like in a pharmaceutically acceptable dosage form. The dosage form may be a solid, semi-solid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical preparations containing a compound of the formula I in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or poly-vinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the person skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or poly-ethylene glycol. Hard gelatine capsules may contain granules of the active substance using either the abovementioned excipients for tablets e.g. lactose, saccharose, sorbitol, mannitol, starches (e.g. potato starch, corn starch or amylopectin), cellulose derivatives or gelatine. Also liquids or semi-solids containing the drug can be filled into hard gelatine capsules.

Dosage units for rectal administration can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral administration may be in the form of syrups or suspensions, for example solutions containing from about 0.2% to about 20% by weight of the active substance herein described, the balance being made up by sugar and/or mixtures of ethanol, water, glycerol, and propylene glycol. Optionally such liquid preparations may contain colouring agents, flayouting agents, saccharine and carboxymethyl-cellulose as thickening agents or other excipients known to the person in the art.

Solutions for parenteral administration by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

Suitable daily doses of the compounds of the invention in therapeutical treatment of humans are about 0.01–100 mg/kg bodyweight at peroral administration and 0.001–100 mg/kg bodyweight at parenteral administration.

Synthetic Methods

The compounds according to the invention may be obtained, i.a., from p-fluorophenol or p-chlorophenol via the corresponding 3-chloropropionates or acrylates (for example, compounds I, XII and XXIII) which undergo Fries rearrangement followed by a Friedel-Crafts type ring closure to give 7-hydroxy-1-indanones (e.g., compounds II and XIII). The indanones are O-methylated to yield methyl ethers (e.g., compounds III and XIV) and, by a Wittig reaction, converted to the corresponding 2-methylene-indans (e.g., compounds IV and XV) which are oxidatively rearranged under catalysis by Thallium(III)nitrate to give 5-fluoro or 5-chloro-8-methoxy-2-tetralones (e.g., compounds V and XVI). The tetralones are converted to 2-benzylaminotetralins (e.g., compounds VI and XVII) by reduction with sodium cyanoborohydride of their Schiff bases obtained by condensation with benzylamine. From there, several routes to the 5-fluoro or 5-chloro-8-methoxy-2-(dialkylamino)tetralins (e.g., compounds VIII and XIX) may be pursued.

A first route leads via the corresponding 2-benzylalkylamino tetralins (e.g., compounds XI and XXII) by hydrogenative removal of the benzyl group to monoalkylaminotetralins (e.g., compounds IX and XX) and, from there, by exhaustive alkylation to the respective dialkylaminotetralins.

A second route leads by reductive removal of the benzyl substituent to the 2-aminotetralins (e.g., compounds VII and XVII) which are dialkylated to give the said dialkylaminotetralins.

The last step of the synthesis entails the removal of the O-methyl group by boiling with concentrated hydrobromic acid giving the respective 5-fluoro or 5-chloro-8-hydroxy-2-(dialkylamino)tetralins (e.g., compounds X and XXI).

The compounds according to the invention are obtained either in free form or in form of their salts. Each base may be transferred into the corresponding acid addition salt, preferably by use of a therapeutically acceptable acid or an ion exchanger. Salts which are obtained according to the invention may be transferred into the corresponding free bases, e.g. by using a stronger base or an ion exchanger. Since there is such a close relationship chemically between the free base and its salts, it is natural to consider both even if only one of them is being identified. Compounds according to the invention are sometimes obtained on crystallization in form of their hydrates with varying water content.

Since most of the intermediate amino compounds as well as the end products are sensitive to oxygen, reactions are generally carried out under nitrogen. Preferebly, the compounds according to the invention are stored in form of their addition salts, in the first hand their hydrochlorides or hydrobromides.

The compounds according to the invention containing an asymmetric carbon atom adjacent to the amino group (which may be non-alkylated, monoalkylated or dialkylated) may be resolved into their optical antipodes by known methods. This has been exemplified by the resolution of racemic compound VI with L-tartaric acid.

EXAMPLE 1

4'-fluorophenyl-3-chloropropionate (I)

3-Chloropropionyl chloride (391.5 g) and 3 drops of triethylamine is added to 4-fluorophenol (308.3 g) under stirring at 60° C. After heating to 100° C. for 1.5 hrs, distillation gives 544.7 g of (I) boiling at 126°–130° C. 10 mm Hg.

4-fluoro-7-hydroxy-1-indanone (II)

Compound I (219 g) is slowly added to anhydrous AlCl$_3$ (720 g) under nitrogen and kept at room temperature while stirred. Stirring is discontinued when the mixture becomes too viscous. After heating to 120° C. for 1 h, stirring is re-started again and the temperature is further increased to 180° C. (2 hrs). After cooling and addition of excess water, the product is steam-distilled. Extraction with chloroform and evaporation gives 127 g of crude II.

4-fluoro-7-methoxy-1-indanone (III)

In a nitrogen atmosphere, to 300 g powdered potassium carbonate in 1.5 l of acetone is added 121 g II under stirring, followed by 83 ml of dimethyl sulphate. After heating to reflux for 2 hrs, the solvent is distilled off, water is added and the mixture refluxed for a further hour. Extraction with methylene chloride and evaporation gives 125 g of crude III, which is purified by crystallization from EtOAc, m.p. 118°–120°.

5-fluoro-8-methoxy-2-tetralone (V)

NaH (6.8 g) suspended in dimethyl sulfoxide (40 ml) under nitrogen is heated to 80° C. for 1 h. A further 40 ml dimethyl sulfoxide and then 80 g of methyltriphenylphosphonium bromide is added in portions. After stirring for 15 min, 20 g III, partially suspended in 40 ml dimethylsulfoxide, is added and the mixture heated to 70° C. overnight. Pouring the mixture onto ice + hexane followed by extraction with hexane gives 17.6 g of crude 4-fluoro-7-methoxy-1-methyleneindan (IV) which was dissolved in 70 ml MeOH. This solution is added to a stirred solution of the trihydrate of thallium trinitrate (43.9 g) in 400 ml of MeOH and $HC(OCH_3)_3$. After stirring for 1 min, 200 ml chloroform is added at once. Washing with aqueous sodium bicarbonate, drying and concentrating gives a crude product which is purified by chromatography (silica, diethyl ether-hexane 1:1). The resulting mixture of V and its dimethylketal is hydrolyzed with 1 M HCl-diethyl ether to give 11.8 g V. $^1$H NMR (chloroform-$d_1$) δ 7.02–6.64 (m, 2H); 3.79 (s, 3H); 3.51 (s, 2H); 3.10 (t, 2H); 2.56 (t, 2H).

(±)-2-Benzylamino,5-fluoro-8-methoxytetralin [(±)-VI]

Benzylamine (13.4 ml) is added to 500 ml benzene and 11.8 g V under $N_2$.

After keeping at reflux overnight, water is removed by azeotropic distillation. The crude reaction mixture is evaporated and then dissolved in 500 ml methanol. The pH is adjusted to 3–4 by addition of HCl/MeOH.

$NaCNBH_3$ (2.36 g) is added and the mixture stirred under $N_2$ for 2 hrs, the pH being kept at 3–4 by addition of HCl/MeOH or triethylamine. After concentrating 5 M aqueous HCl is added and the precipitate filtered off and washed with diethyl ether. Conversion to the free base (±)-VI is effected by treatment with 1 M NaOH/diethyl ether. Purification by chromatography on alumina (diethyl ether/light petroleum 1:2) gives 12.4 g of the free base (±)-VI.

Resolution of (±)-VI (+)-L-tartaric acid (9.08 g) is added to (±-VI (17.25 g) in 1050 ml of hot 95% ethanol. The solution is kept at room temperature overnight, and the resulting crystals (7.25 g) are recrystallized from EtOH. Treatment with 5 M NaOH gives the free amine which is extracted with diethyl ether. It is converted into the hydrochloride which is recrystallized from MeOH/diethyl ether to give 3.88 g of (+)-VI·HCl. $^1$H NMR (methanol-$d_4$); δ7.60–7.40 (m, 5H), 7.05–6.65 (m,2H), 4.35 (s, 2H), 3.82 (s, 3H), 3.7–1.6 (m, 7H). Optical rotation ($[\alpha]_D$ 22, MeOH, as in all following determinations): +61.4° (c, 1.0). Enantiomeric excess determined by capillary GC of the (R)-2-methoxy-2-phenylacetamides (ee) is 99.7%.

The free amine (11.77 g) isolated from the mother liquors from the preparation of (+)-VI is added (−)-D-tartaric acid (6.19 g). The procedure used to obtain (−)-VI·HCl 4.93 g is essentially the same as above.

(+)-2-Amino-5-fluoro-8-methoxytetralin hydrochloride [(+)-VII·HCl]

(+)-VI·HCl (1.63 g) is dissolved in 100 ml of MeOH. Catalytic hydrogenation over Pd/C gives 1.14 g of (+)-VII·HCl, m.p. 261°–263° C. Optical rotation: +67.8° (c,

(−)-2-Amino-5-fluoro-8-methoxytetralin hydrochloride [-(−)-VII·HCl]

Prepared as described for (+)-VII·HCl but starting from (−)-VI·HCl. Yield 99%, m.p. 262°–264°; Optical rotation: −67.2° (c 1.0).

(+)-5-Fluoro-8-methoxy-2-(dipropylamino)tetralin hydrochloride [(+)-VIII·HCl]

1-iodopropane (0.89 ml) is added to a mixture of (+)-VII·HCl (1.01 g) and powdered potassium carbonate in 30 ml MeCN under nitrogen. The mixture is stirred at room temperature for 10 days during which two portions of 0.3 ml 1-iodopropane is added. After addition of diethyl ether, filtration and evaporation, the crude product purified by chromatography on alumina (diethyl ether/light petroleum, 1:4) to give 0.90 g of (+)-VIII·HCl and, on further elution, 0.23 g of (+)-5-fluoro-8-methoxy-2-propylaminotetralin hydrochloride, (+)-XI·HCl.

Yield 71%. Repeated recrystallization gives pure (+)-VIII, m.p. 134°–135°. Optical rotation: +78.9° (c 1.0).

(−)-5-Fluoro-8-methoxy-2-(dipropylamino)tetralin hydrochloride [(−)-VII·HCl]

Prepared as described for (+)-VIII·HCl but starting from (−)-VII·HCl. Yield 80%, m.p. 134°–135°. Optical rotation: −78.4° (c 1.0).

(+)-5-Fluoro-8-hydroxy-2-(dipropylamino)tetralin hydrobromide [(+)-X·HBr]

All equipment is carefully washed with concentrated sulfuric acid before the start of the reaction. (+)-VIII·HCl (98 mg) is added to (47%) aqueous HBr and refluxed under $N_2$ for 2 hrs. The acid is driven off in vacuo at 100°. Then, twice, diethyl ether is added and to removed by evaporation. Recrystallization from MeOH/diethyl ether gives 75 mg (69%) of (+)-X·HBr, m.p. 186°–187°. Optical rotation: +69.4° (c 0.9).

(−)-5-Fluoro-8-hydroxy-2-(dipropylamino)tetralin hydrobromide [(−)-X·HBr]

Prepared as described for (+)-X·HBr. Yield 85%, m.p. 186°–187°. Optical rotation: −69.3° (c 1.0).

(+)-2-(N-benzyl-N-propylamino)-5-fluoro-8-methoxytetralin hydrochloride, (+)-XI·HCl 0.13 ml of 1-iodopropane is added to a mixture of (+)-VI (0.41 g) and powdered potassium carbonate (1.22 g) in 10 ml $CH_3CN$. The mixture is stirred at room temperature under nitrogen for 31 days. Additional 1-iodopropane (1.6 ml) is added in portions during this period. Workup as described for (+)-VIII yields 211 mg of (+)-XI·HCl, m.p. 152°–153° by crystallization from methanol/diethyl ether. Optical rotation: +78.7° (c 1.0).

(−)-2-(N-benzyl-N-propylamino)-5-fluoro-8-methoxytetralin hydrochloride, (−)-XI·HCl is synthesized in the same manner as (+)-XI·HCl, but with (−)-VI as starting material. It crystallizes from EtOH-diethyl ether as a hemihydrate, m.p. 124°–130°. Optical rotation: −79.6° (c 1.0).

(−)-5-Fluoro-8-methoxy-2-propylaminotetralin hydrochloride, (−)-IX·HCl (−)-XI·HCl (1.93 g) was dissolved in 100 ml of MeOH and hydrogenated over Pd/C. Yield of (−)-

IX·HCl 0.75 g, m.p. 208°–210° (EtOH/diethyl ether). Optical rotation: −71.5° (c 1.0).

(+)-XI·HCl was prepared in the same way, but starting from (+)-XI·HCl, m.p. 207°–210° (EtOH/diethyl ether).

(−)-VIII·HCl from (−)-IX·HCl

The reaction was carried out in essentially the same way as the alkylation of (−)-VI with iodopropane described above.

EXAMPLE 2

(±)-5-Fluoro-8-hydroxy-2-(dipropylamino)tetralin hydrobromide, (±)-X was prepared analogously to the hydrobromides of (+)-X and (−)-X from copound (±)-VI. M.p. 201°–203° C. after crystallization from EtOH/diethyl ether. Intermediate (±)-VII was transformed without prior purification into (±)-VIII which crystallised with ¼ molecule of water from EtOH/diethyl ether, m.p.146°–147° C.

EXAMPLE 3

(±)-5-Chloro-8-hydroxy-2-(dipropylamino)tetralin hydrochloride, (±)-XXI·HCl is prepared in analogy to the preparation of (±)-X but starting from 4′-chlorophenyl-3-chloropropionate (XXIII) obtained by the reaction of 4-chlorophenol with 3-chloro-propionyl chloride. XXIII is a colourless liquid with b.p. 155°–159° C. at 10 mm Hg; yield 94%. (±)-XXI·HCl has m-p- 229°–231° C. (recrystallized from MeOH/diethyl ether.

4-Chloro-7-hydroxy, 1-indanone (XIII) is obtained from XXIII in essentially the same way as the corresponding fluoro compound II. Crystals directly collected from the steam distillate,. m.p. 119°–121° C.; yield 74%.

4-Chloro-7-methoxy-1-indanone (XIV). Procedure as for preparation of III. M.p. 139°–141° C. Yield 82%.

5-Chloro-8-methoxy-2-tetralone (XVI) is prepared via the methyleneindan XV (88 % yield) according to the method described for the synthesis of V. Yield from XV 98%. $^1$H NMR (methanol-d$_4$): 67 7.25 (d, 1H); 6.70 (d,1H); 3.81 (m, 3H); 3.51 (s, 2H); 3.20 (t, 2H); 2.57 {t, 2H).

(±) -5-Chloro-8-methoxy-2-(propylamino) tetralin hydrochloride (±)-XVI. 5.1 g of (±)-XVI is dissolved in 250 ml of dry benzene, and 2.8 g of 1-propylamine is added. The mixture is refluxed for 2 hrs in a Dien-Stark apparatus. After concentration of the reaction mixture, the resulting imine is dissolved in 200 ml EtOH and hydrogenated over PtO$_2$. Working up and transferring to the free amine with 5 M NaOH/diethyl ether followed by chromatography on alumina with diethyl ether as eluent yields 4.45 g of the corresponding hydrochloride after addition of HCl in diethyl ether. M.p. 244°–245° C. Crystallizes as hemihydrate from methanol/diethyl ether.

(±)-5-Chloro-8-methoxy-2-dipropylamino)tetralin hydrochloride, (±)-XIX. 1-Iodopropane (0.84 ml) is added to a mixture of the hydrochloride of XVI (2.00 g) and powdered potassium carbonate (5.48 g) in 20 ml of methyl cyanide under nitrogen. The mixture is stirred at room temperature for 8 days. A further 0.66 ml of the iodopropane is added in portions during that time. Working up similarly as described for the fluoro analogue gives 61% of (±)-XIX as the hydrochloride. M.p.160–161 C. It is used for the preparation of (±)-XXI (Yield 59%) by dehydrobromination carried out in the same way as described above.

We claim:

1. A S-enantiomer of a compound of the formula

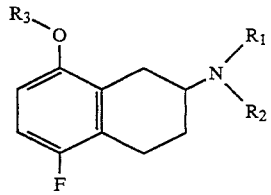

wherein
R$_1$ is H, C$_1$–C$_6$ alkyl or cyclic C$_3$–C$_6$ alkyl,
R$_2$ is H, C$_1$–C$_6$ alkyl or cyclic C$_3$–C$_6$alkyl,
R$_3$ is H, C$_1$–C$_6$ alkyl or cyclic C$_3$–C$_6$ alkyl,
and wherein C$_1$–C$_6$ alkyl represents straight, and branched alkyl groups having 1 to 6 carbon atoms or salt thereof.

2. A S enantiomer according to claim 1, wherein R$_2$, and R$_3$ are, independently, alkyl and are selected from methyl, ethyl, n-propyl, and n-butyl.

3. A S enantioner according to claim 1, wherein R$_1$ and R$_2$ are n-propyl and R$_3$ is H.

4. A S enantiomer according to claim 1, wherein R$_1$ and R$_2$ are n-propyl and R$_3$ is methyl.

5. A pharmaceutically acceptable salt of a S enantiomer according to any one of claims 1–4.

6. A pharmaceutical preparation comprising a S-enantiomer of a compound of the formula I

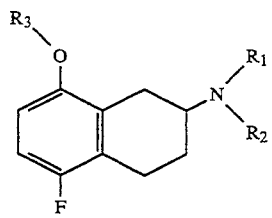

wherein
R$_1$ is H, C$_1$–C$_6$ alkyl or cyclic C$_3$–C$_6$ alkyl,
R$_2$ is H, C$_1$–C$_6$ alkyl or cyclic C$_3$–C$_6$ alkyl,
R$_3$ is H, C$_1$–C$_6$ alkyl or cyclic C$_3$–C$_6$ alkyl,
and wherein C$_1$–C$_6$ alkyl represents straight, and branched alkyl groups having 1 to 6 carbon atoms or a pharmaceutically acceptable salt of said S-enantiomer; and a pharmaceutically acceptable carrier.

7. A pharmaceutical preparation according to claim 6, wherein R$_1$, R$_2$, and R$_3$ are, independently, alkyl and are selected from methyl, ethyl, n-propyl, and n-butyl.

8. A pharmaceutical preparation according to claim 6, wherein R$_1$ and R$_2$ are n-propyl and R$_3$ is H.

9. A pharmaceutical preparation according to claim 6, wherein R1 and R$_2$ are n-propyl and R$_3$ is methyl.

10. A method for treatment of disorders in the central nervous system, especially 5-hydroxytryptamine mediated disorders, comprising administering to a mammal a suitable amount off the pharmaceutical preparation according to any one of claims 6–9.

11. A method for treatment of depression, anxiety, anorexia, senile dementia, migraine, Alzheimer's disease, thermoregulator and sexual disturbances comprising administering to a mammal a suitable amount of the pharmaceutical preparation according to any one of claims 6–9.

12. A method for treatment of pain comprising administering to a mammal a suitable amount of the pharmaceutical preparation according to any one of claims 6–9.

13. A method for treatment of disturbances in the cardiovascular system comprising administering to a mammal a suitable amount of the pharmaceutical preparation according to any one of claims 6–9.

* * * * *